United States Patent
Zafred et al.

(10) Patent No.: US 10,241,018 B2
(45) Date of Patent: Mar. 26, 2019

(54) WEAR TEST APPARATUS

(71) Applicant: United States Department of Energy, Washington, DC (US)

(72) Inventors: Paolo R. Zafred, Murrysville, PA (US); William H. Howland, Wexford, PA (US)

(73) Assignee: U.S. Department of Energy, Washington, DC (US)

( * ) Notice: Subject to any disclaimer, the term of this patent is extended or adjusted under 35 U.S.C. 154(b) by 225 days.

(21) Appl. No.: 15/335,542

(22) Filed: Oct. 27, 2016

(65) Prior Publication Data

US 2017/0153171 A1 Jun. 1, 2017

Related U.S. Application Data

(60) Provisional application No. 62/247,453, filed on Oct. 28, 2015.

(51) Int. Cl.
*G01N 3/56* (2006.01)
*G01N 3/32* (2006.01)

(52) U.S. Cl.
CPC ............. *G01N 3/56* (2013.01); *G01N 3/32* (2013.01); *G01N 2203/0005* (2013.01); *G01N 2203/0008* (2013.01); *G01N 2203/023* (2013.01); *G01N 2203/0222* (2013.01); *G01N 2203/0224* (2013.01); *G01N 2203/0232* (2013.01)

(58) Field of Classification Search
CPC .... G01N 3/56; G01N 3/32; G01N 2203/0005; G01N 2203/0008; G01N 2203/0222; G01N 2203/0224; G01N 2203/023; G01N 2203/0232
See application file for complete search history.

(56) References Cited

U.S. PATENT DOCUMENTS

| 5,007,284 A * | 4/1991 | Slone ................. G01M 13/005 73/114.78 |
| 6,546,782 B1 * | 4/2003 | De La Cruz ............ G01N 3/56 73/10 |
| 9,194,784 B1 * | 11/2015 | Bi ............................ G01N 3/56 |
| 2007/0017300 A1 * | 1/2007 | Bushey .................... G01N 3/02 73/856 |

FOREIGN PATENT DOCUMENTS

CN 204142594 * 2/2015 ............ G01N 3/56

* cited by examiner

*Primary Examiner* — Eric S. McCall
*Assistant Examiner* — Timothy P Graves
(74) *Attorney, Agent, or Firm* — Robert T. Burns; Jennifer R. Mahalingappa; Brian J. Lally

(57) ABSTRACT

Disclosed is an exemplary test apparatus having an autoclave head, a fretting mechanism connected on a first end to a first side of the autoclave head, a load train operably connected with a first end of the fretting mechanism, an autoclave adapter connected on a first side to a second side of the autoclave head, and a force balance assembly connected to a second side of the autoclave head and configured to equalize a pressure acting on the load train. Certain exemplary embodiments include an upper plate, a plurality of upper tie rods connected to a first side of the upper plate and a second side of the autoclave adapter, a lower plate, a plurality of lower tie rods connected to the first side of the autoclave head and a first side of the lower plate, and a pressure vessel sealingly connected to the first side of the autoclave head.

17 Claims, 13 Drawing Sheets

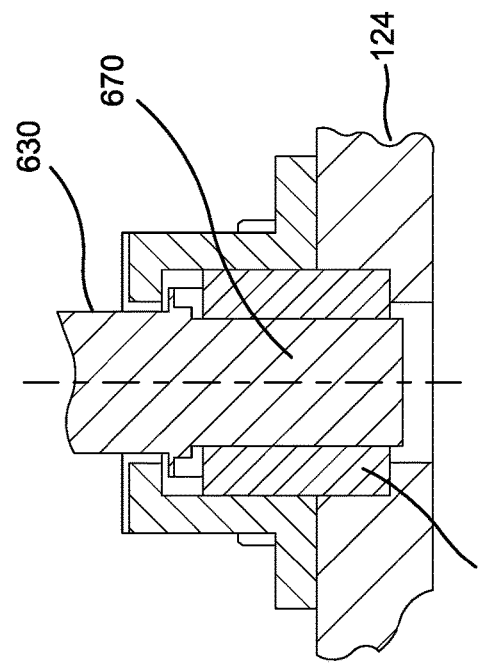
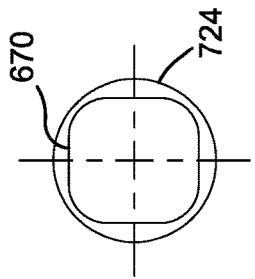
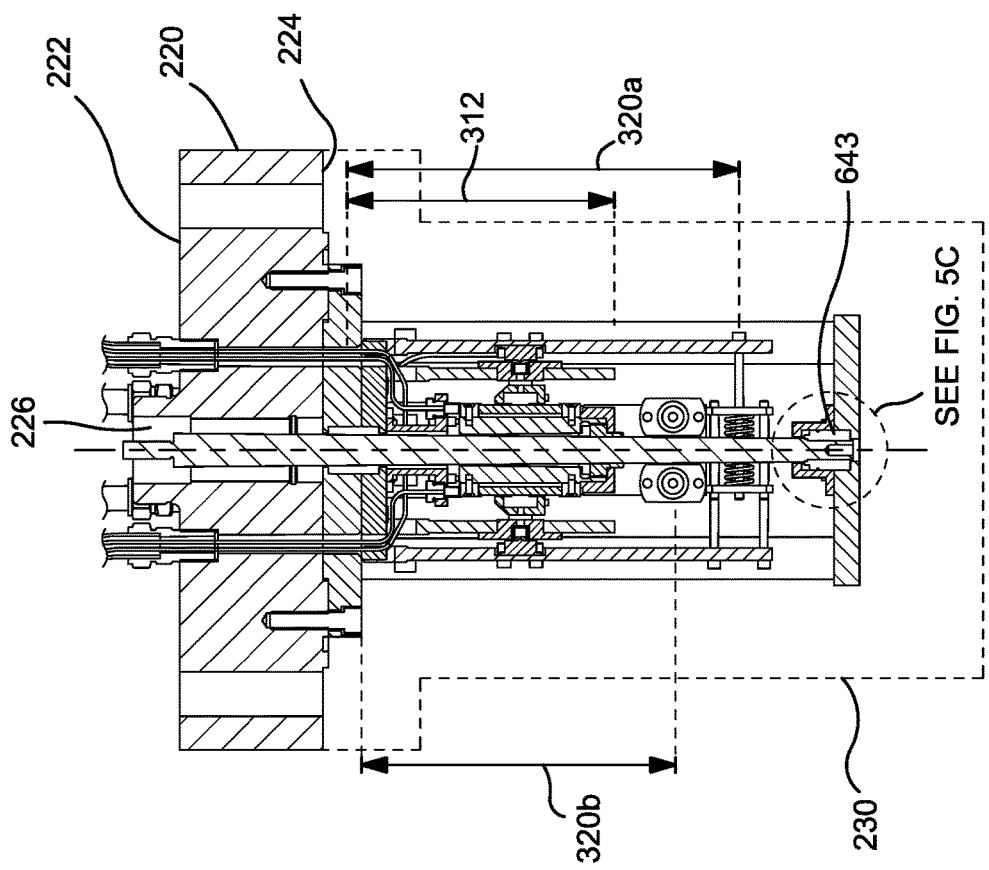
FIG. 5C
FIG. 5D
FIG. 5B

WEAR TEST APPARATUS

PRIORITY CLAIM

The present Patent Application claims priority under 35 U.S.C. § 119(e) to Provisional Patent Application No. 62/247,453 filed Oct. 28, 2015, the contents of which are hereby incorporated by reference in their entirety.

GOVERNMENT INTEREST STATEMENT

This invention was made with government support under DOE Contract No. DE-NR0000031 and Navy Contract No. N00024-08-C-2103. The government has certain rights in the invention.

BACKGROUND

Field

This present subject matter relates generally to an apparatus and method for measuring the wear rate of materials in a high-temperature pressurized environment.

Background

A number of fretting wear machines exist for bench testing material specimens subjected to reciprocating motion. As defined herein, fretting includes high frequency (>20 Hz), low amplitude (10-125 μm) motion, and sliding includes low frequency (1-10 Hz), high amplitude (125-500 μm) motion to test one or more samples pairs in one or more of a fretting and/or sliding motion configuration. These machines are typically configured as pin on disc, ball on flat, block on ring, crossed cylinders, or sliding ball test rigs. Selection will depend on the type of test performed, sample configuration, and/or the specific application. Some of these machines are disclosed in U.S. Pat. No. 3,945,241 (Brown); U.S. Pat. No. 5,375,451 (Sandstrom); U.S. Pat. No. 5,969,226 (Wert); and U.S. Pat. No. 6,601,456 (Davidson).

One drawback of these machines is that they can only test one wear couple at a time, and are generally unsuitable for operation in a pressurized, high temperature environment. They are limited to reciprocating tests in air using simple geometry stationary specimens loaded with dead weights placed on top of the specimen to generate the normal load. Additionally, measuring only one wear couple at a time precludes accurate comparisons between the specimen of interest and its associated control specimen. The most common actuation method used to generate reciprocating motion is a mechanical linkage, where motor rotation is converted into small scale linear displacements. Other methods include eccentric cams and followers, with a rotating shaft in conjunction with a cam action generating oscillatory motion.

With these configurations only discrete displacements are attainable, with stroke length typically adjusted by manually replacing a cam. It is difficult to control displacements at mid-stroke position with existing fretting machines. It is also difficult in machines equipped with cams and followers, which lack a device to control and adjust stroke length while they are running. Further, these devices lack the capability to allow precise adjustment (repeatable positioning to ±2 microns in certain embodiments for aligning wear contact surfaces and/or positioning specimens at a desired mid-stroke (reference) position) or stroke amplitude to compensate for backlash or thermal expansion of the load train while the machine is running.

Although mechanical drive systems having mechanical linkages and cams can provide a simple and cost effective means of stroke actuation, they lack the necessary stiffness for preventing parasitic displacement leading to "false fretting" where the displacement or a significant portion of specimen displacement is reduced by unintended slack in the system. Existing devices have clearances and stiffnesses which, even under moderate loads, mask displacements of 10-125 microns. It is therefore necessary to ensure that machine stiffness is high enough to prevent parasitic displacement leading to "false fretting" where the displacement or a significant portion thereof is masked by unintended machine movement.

Other actuators, such as piezo-electric, electro-magnetic and magnetostrictive actuators, also have significant drawbacks. Piezo-electric actuators, for example, can operate at high frequency but are limited to very small displacement and forces, with displacement limited to approximately 20-80 microns, and force limited to approximately 500-1000 lbf. They can be a cost effective means of actuation for low load applications, with the benefit that the inertia of moving components is very low, therefore minimizing out of balance forces and the need for a high mass fretting wear machine. These benefits come at a design cost, however. In a piezo-electric actuator, for example, force generation is inversely proportional to displacement. Therefore, when force generation is maximum displacement drops to zero. Conversely, at full displacement, no force is generated. Another disadvantage is that the stroke of a piezo-electric actuator is directly proportional to applied voltage. As the stroke of the actuator increases, so does the required voltage, typically from 1-2 kV, making piezo-electric actuators unsuitable for large-scale devices.

Electro-magnetic oscillators are also used as actuators in fretting machines, but they too have their disadvantages. Electro-magnetic oscillators are force generators rather than displacement generators. Because the resisting (frictional) force changes as the test progresses, the loop gain of the system varies, altering the system response. Even though an electro-magnetic actuator is operated with positional feedback, the positional control loop is in cascade with the primary force loop. This makes controlling amplitude and stroke mid position problematic.

Still other fretting machines use magnetostrictive actuators. These actuators rely on new rare earth alloys (e.g. Terfenol-D and/or Galfenol) placed in a magnetic field aligned with the material's magnetostrictive axis. When a DC current is applied, the material proportionally expands, converting electric energy into mechanical motion. They require more power than piezo-electric actuators and cannot generate the same levels of displacement and force as servo-hydraulic actuators.

Thus, while a number of fretting machines designed to perform wear testing in air have been developed for research applications, few can operate in a wide range of fretting parameters, and none are suitable for multi-specimen or autoclave environment testing. A need exists for a fretting machine which overcomes one or more of the limitations described above.

SUMMARY

Disclosed is an exemplary test apparatus having an autoclave head, a fretting mechanism connected on a first end to a first side of the autoclave head, a load train operably connected with a first end of the fretting mechanism, an autoclave adapter connected on a first side to a second side of the autoclave head, and a force balance assembly connected to a second side of the autoclave head and configured to equalize a pressure acting on the load train. Certain exemplary embodiments include an upper plate, a plurality of upper tie rods connected to a first side of the upper plate and a second side of the autoclave adapter, a lower plate, a plurality of lower tie rods connected to the first side of the autoclave head and a first side of the lower plate, and a pressure vessel sealingly connected to the first side of the autoclave head.

Also disclosed is an exemplary method of testing fretting wear, which includes the steps of placing a test sample in a fretting mechanism, the mechanism having a holder station configured to connect to a load train and having at least two sample holders, contacting the test sample with an opposing sample in an opposing sample holder, and applying a reciprocating motion to the test sample with the test sample in contact with the opposing sample. Certain exemplary methods further include the step of varying at least one of a frequency, force, and stroke length of the reciprocating motion. Still other exemplary methods include the step of placing the test sample in a pressurized environment, while yet other exemplary methods include the steps of varying at least one of a pressure and/or temperature of the pressurized environment.

BRIEF DESCRIPTION OF THE DRAWINGS

A description of the present subject matter including various embodiments thereof is presented with reference to the accompanying drawings, the description not meaning to be considered limiting in any matter, wherein:

FIG. 5A-5D illustrate an exemplary force balance assembly, load train, and actuator assembly.

Similar reference numerals and designators in the various figures refer to like elements.

DETAILED DESCRIPTION

Figure 1:
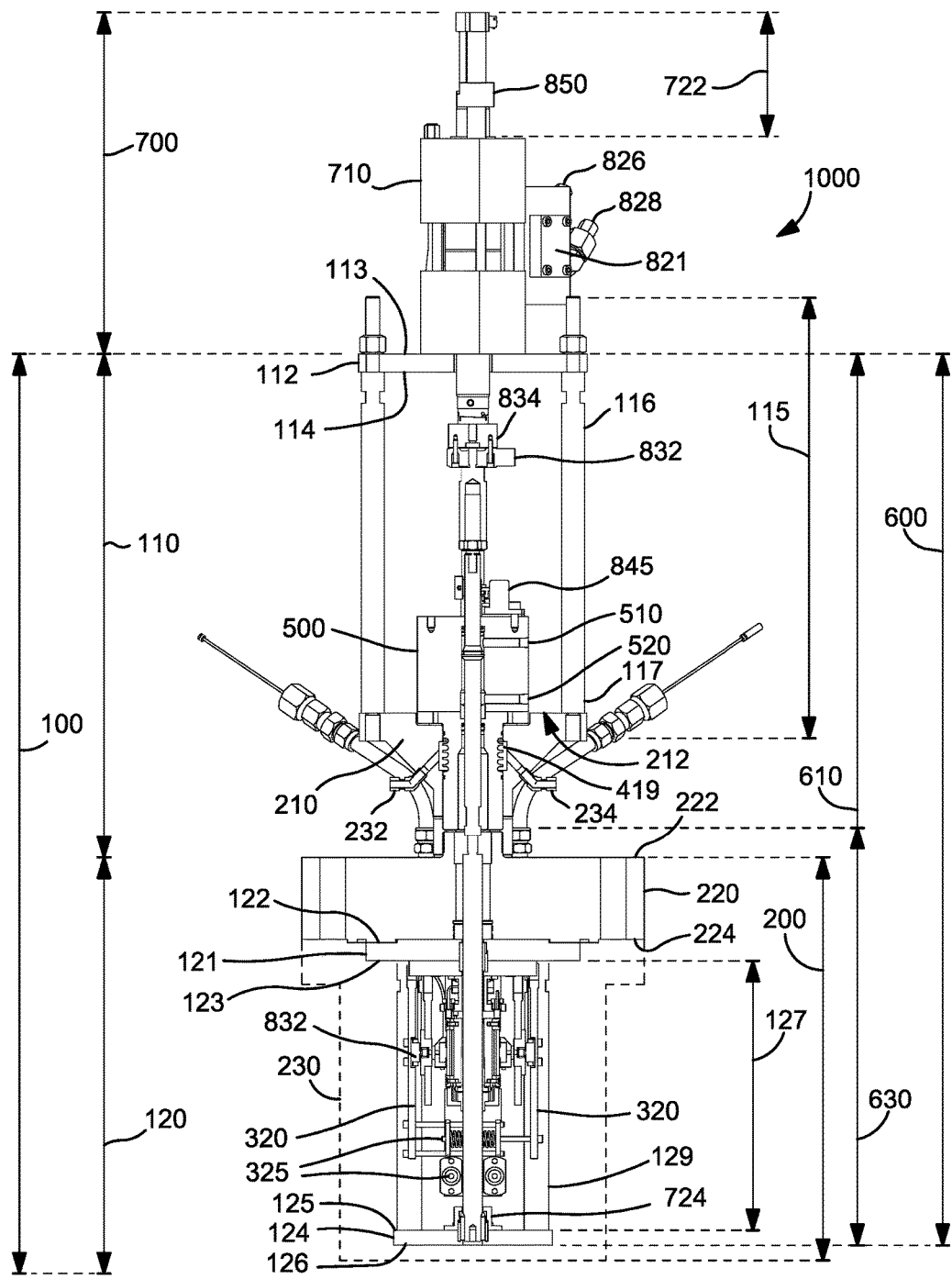
FIGS. 1 and 2 illustrate an exemplary fretting wear test apparatus.
Figure 2:
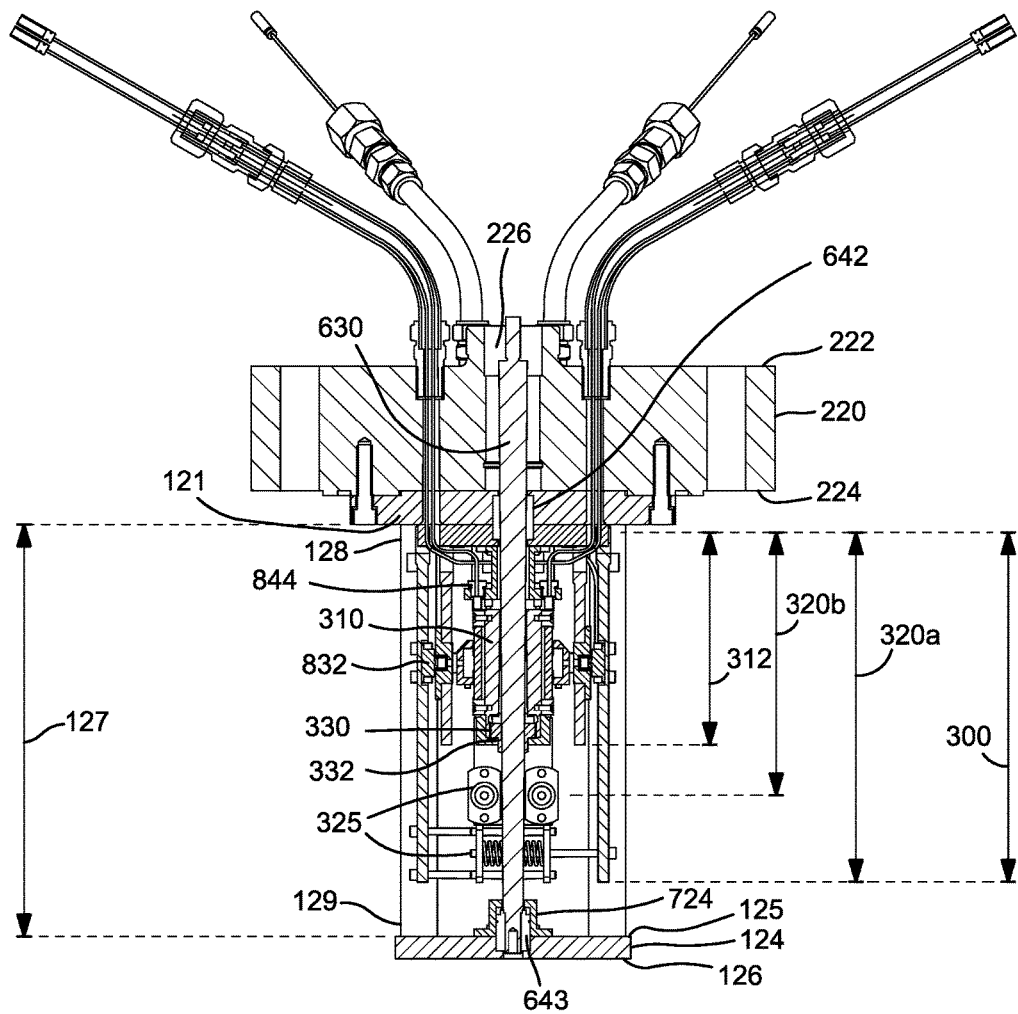

FIGS. 1 and 2 illustrate an exemplary fretting wear test apparatus 1000. The exemplary apparatus of FIGS. 1 and 2 is supported by a support structure 100 which includes upper support structure 110 and lower support structure 120. The upper support structure 110 includes an upper plate 112 and a plurality of upper tie rods 115. The upper tie rods 115 connect at a first end 116 to a first side 113 of upper plate 112 and connect at a second end 117 to an autoclave assembly 200 on a first side 212 of autoclave adapter 210. The second side 214 (shown in FIG. 4) of autoclave adapter 210 connects to the lower support structure 120. In the exemplary embodiment shown, the second side 214 of autoclave adapter 210 connects to an autoclave head 220 on a first side 222 of the autoclave head 220. A plurality of lower tie rods 127 connect on a first end 128 to a first side 122 of intermediate plate 121. A second side 123 of intermediate plate 121 connects to a second side 224 of autoclave head 220. A second end 129 of lower tied rods 127 connect to a first side 125 of a lower plate 124, which also has second side 126. A pressure vessel 230 encloses the lower tie rods 127 and lower plate 124 and sealingly connects with the second side 224 of autoclave head 220. In certain exemplary embodiments the pressure vessel 230 is wrapped in heaters (not shown). Autoclave adapter 210 includes an inlet 232 and discharge 234 (see, e.g., FIG. 5A) for at least one seal system coolant recirculation loop (not shown). The heaters raise the temperature inside pressure vessel 230 to achieve desired conditions. In certain embodiments pressure is maintained at least in part by a pump (not shown) which operates on the principle of pressure intensification.

The exemplary fretting wear test apparatus 1000 includes a fretting mechanism 300 connected on a first end 302 (see, e.g., FIG. 3A) to the autoclave head 220 via intermediate plate 121 and a load train 600 (see, e.g. FIG. 1) operably connected on a load train first end 610 (see, e.g., FIG. 1) (also referred to as upper shaft 610) with fretting mechanism 300 (see, e.g., FIGS. 3A-3H) and configured to connect with an actuator 710 on a second end 304 of fretting mechanism 300 to a load train second end 630 (also referred to as lower shaft 630). The fretting mechanism 300 can but need not be coaxially mounted to the load train 600. The fretting wear test apparatus 1000 further includes force balance assembly 500 connected to a first side 212 of autoclave adapter 210 and configured to equalize a pressure acting on at least a portion of the load train 600 and a pressure vessel 230 sealingly connected to autoclave head 220.

Although the exemplary arrangement of FIGS. 1 and 2 shows certain elements of the test apparatus 1000 configured to be internal to pressure vessel 230 (fretting mechanism 300, for example) and certain elements external to pressure vessel 230 (autoclave adapter 210, force balance assembly 500, and actuator system 700, for example), other configurations can be employed without departing from the scope of the present subject matter. Although not shown, certain embodiments may include a vertically inverted configuration, with the actuator on the bottom and the autoclave on top.

FIGS. 3A-3H illustrate an exemplary embodiment of a fretting mechanism 300. The exemplary embodiment shown includes a holder station 310 (see, e.g., FIG. 3D) having at least two holder station sample holders 311 and configured to connect to load train 600. In certain embodiments holder station 310 is configured for reciprocating motion. The exemplary embodiment shown includes at least two inner arms 312 (see, e.g. FIGS. 3B and 3C), which can but need not be pivoting, and includes at least two opposing inner arm sample holders 313 contacting inner arms 312 and configured to contact with the at least two holder station sample holders 311. The exemplary embodiment also includes at least two external lever arms, such as first external lever arm 320a and second external lever arm 320b (see, e.g. FIGS. 3A-3C), which can but need not be pivoting, configured to contact with the at least two inner arms 312, which can but need not be pivoting. The number of arms and sample holders shown are exemplary only, as other numbers of arms and/or sample holders can be used without departing from the scope of the present subject matter.

The exemplary embodiments shown allow samples to be subjected to different loading and environmental conditions under controlled frequency, amplitude (force), and/or stroke lengths which can, but need not be, varied. In these exemplary embodiments, stationary sample(s) 317a (see, e.g., FIG. 3E) mount to an inner arm sample holders 313 (see, e.g., FIG. 3E), and reciprocating sample(s) 317b (see, e.g., FIG. 3D) mount to the holder station sample holders 311. In other exemplary embodiments the inner and/or outer arms 312/320 can be configured for reciprocating motion, in place of or in addition to the holder station 310 reciprocating motion, without departing from the scope of the present subject matter. In the exemplary embodiment shown, the stationary sample(s) 317a are configured to be in contact with opposing reciprocating sample(s) 317b. This configuration allows surfaces of opposing samples 317a/317b to be frictionally engaged and move in contact with each other, simulating motion in real components and the in-plane dynamic characteristics of typical operating conditions.

Figure 3A:
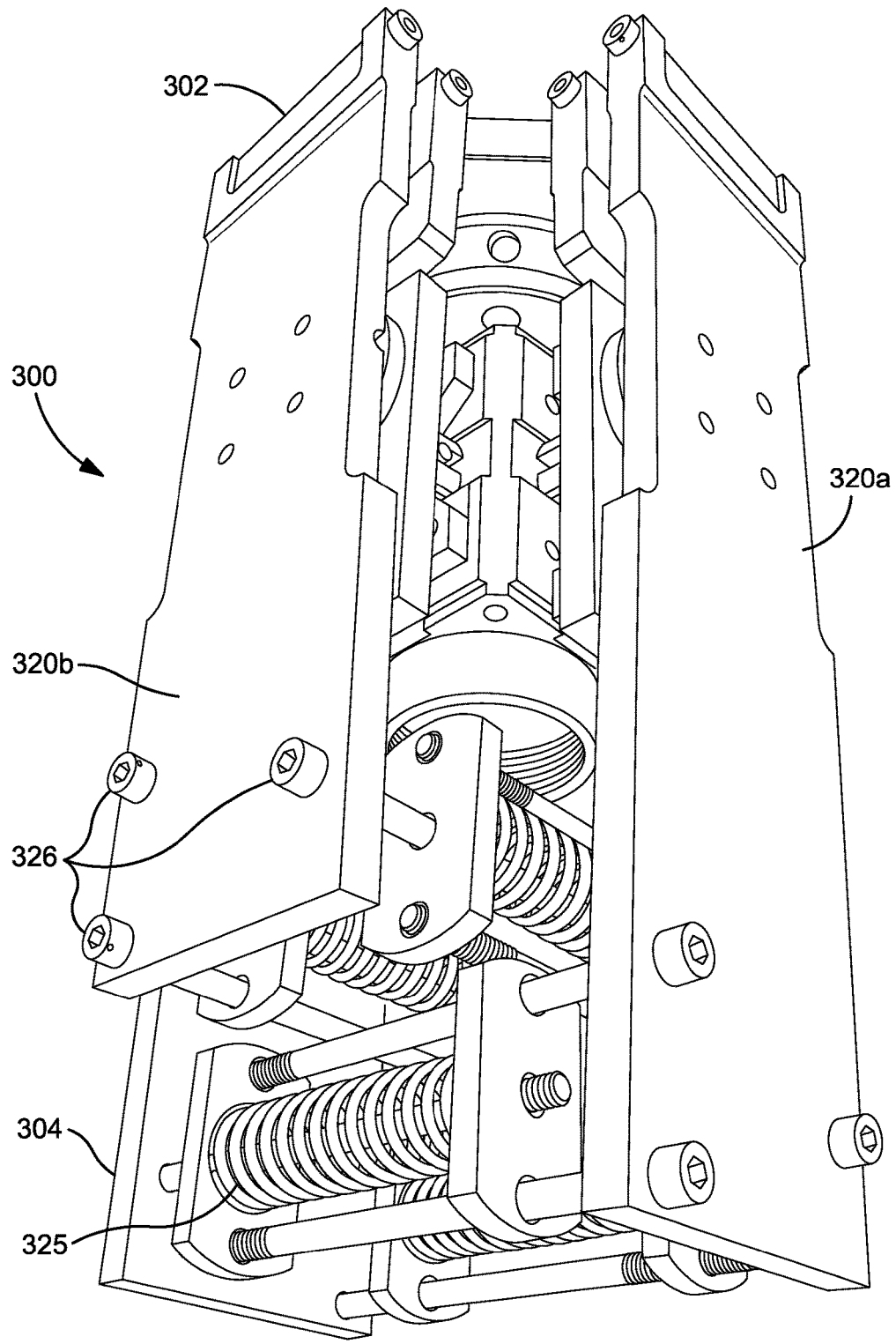
FIGS. 3A-3H illustrate an exemplary fretting mechanism.
Figure 3B:
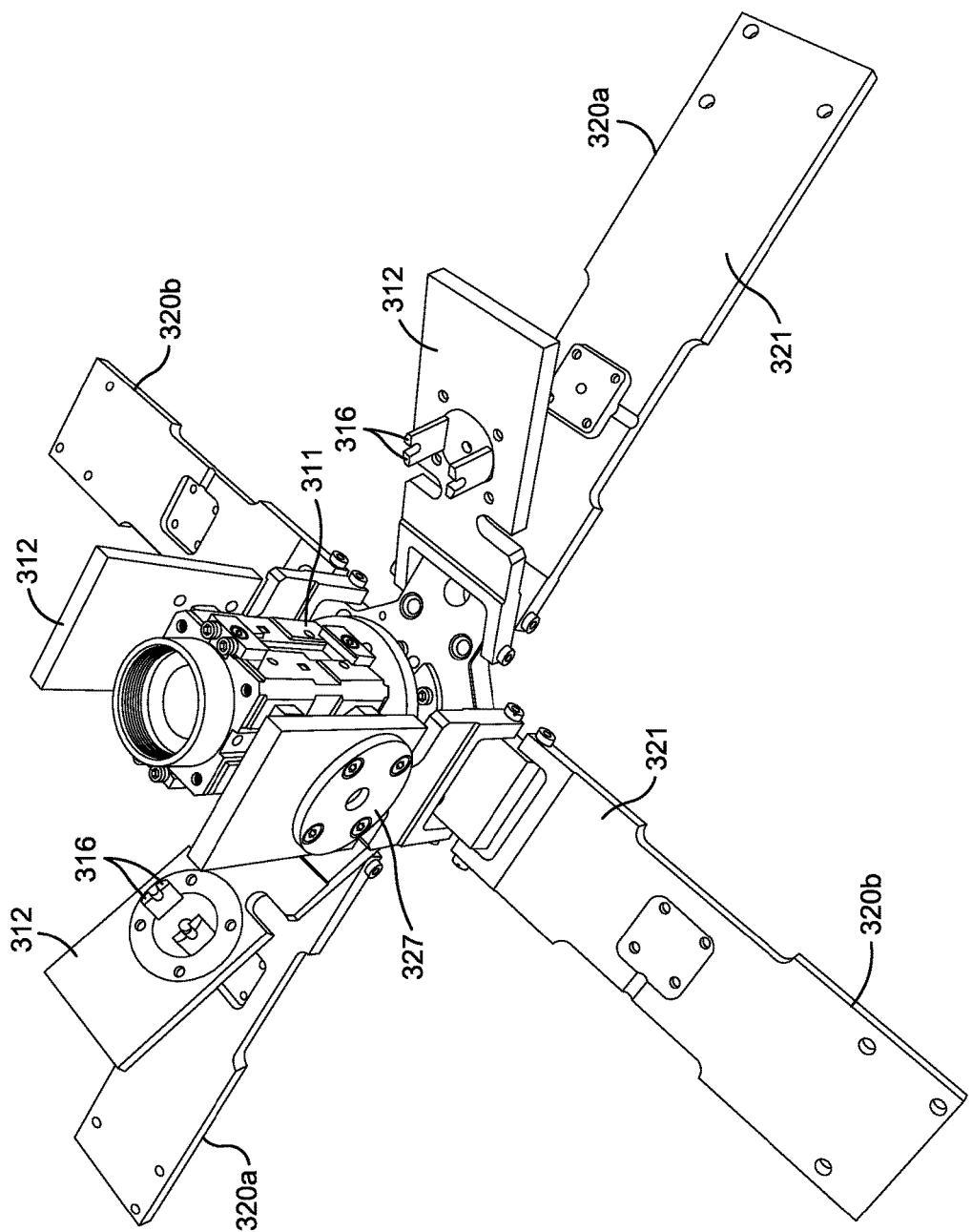
Figure 3C:
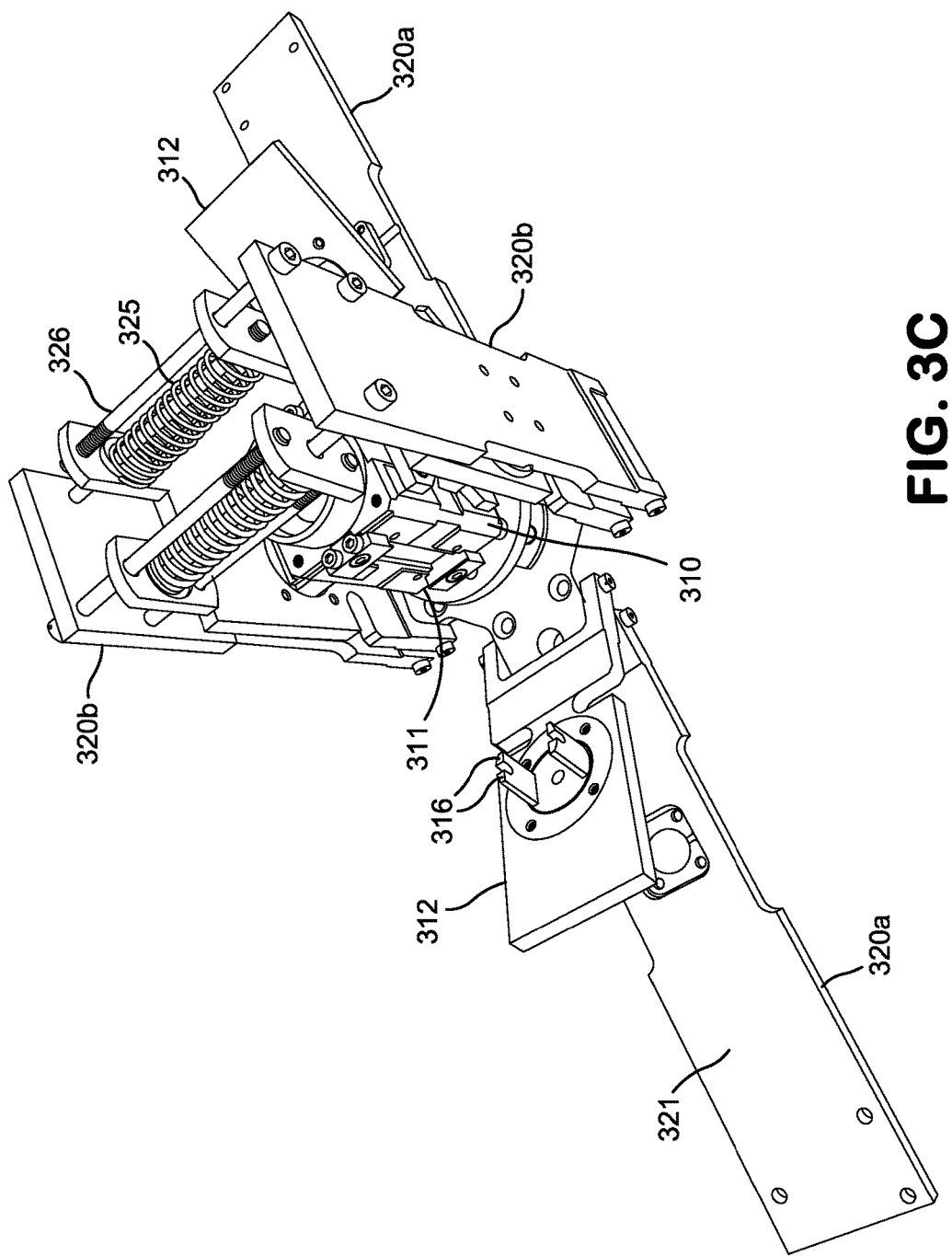
Figure 3D:
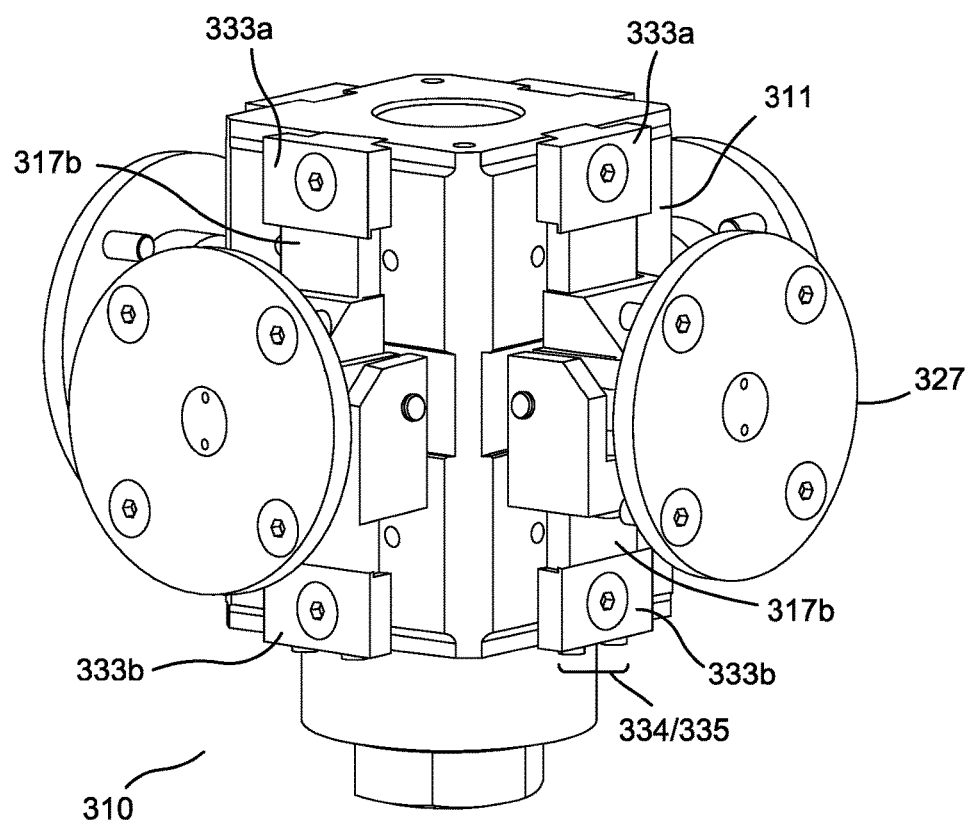
Figure 3E:
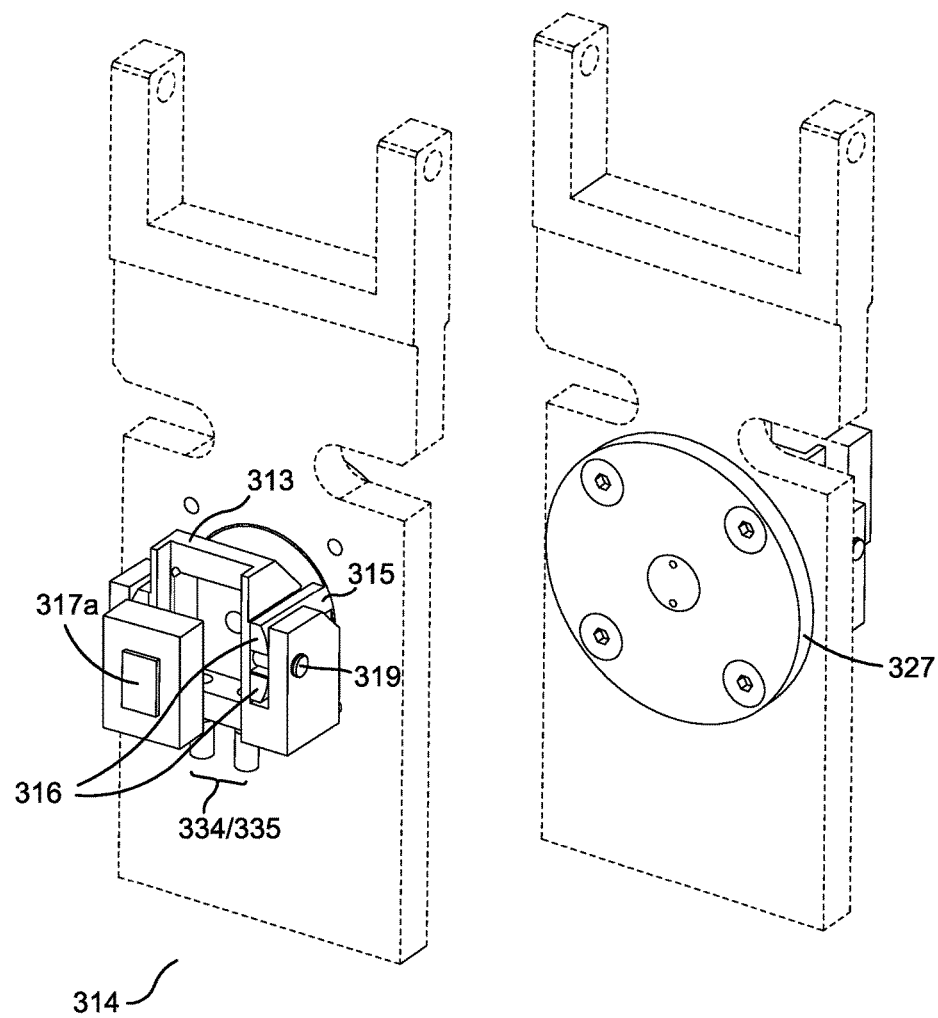

Certain exemplary embodiments of the present subject matter include at least one sample holder assembly 314, with a view of an exemplary sample holder assembly 314 illustrated in FIG. 3E. The exemplary sample holder assembly 314 is shown in a flat-on-flat configuration, though other configurations known to those of skill in the art can be used without departing from the scope of the present subject matter. Other configurations include but are not limited to use of cylindrical specimens and/or ball on-flat or pin-on-disc geometries. In these and other exemplary embodiments, a specific wear factor (SWF) can be calculated from measured parameters to obtain such as fretting amplitude, contact force, number of cycles and environmental conditions for wear couple materials under test. As defined herein, SWF is the volume loss normalized with respect to sliding distance and applied load. Thus with normalization, the SWF can be used to compare tests performed at different experimental conditions.

As shown in FIG. 3E, the exemplary sample holder assembly 314 includes coupler 315 and flange 327. In certain embodiments, coupler 315 includes prongs 316 which form a slot configured to pivotally hold sample holder 313 to facilitate placing and fastening a stationary sample 317*a* in coupler 315. In certain exemplary embodiments, holder 313 pivotally attaches to the coupler 315 in an upright position vertically parallel to holder station sample holder 311. In the exploded view of FIG. 3E, stationary sample 317*a* is shown removed from sample holder 313 with set plungers/screws 334/335 backed off from holder 313. In certain exemplary embodiments, sample holder assembly 314 further includes at least one stationary sample 317*a* configured with a protruding pad to bear against opposing reciprocating sample 317*b*. In these embodiments holder 313 optionally includes a pivot 319 to compensate for any misalignment. The pad is shown as a quadrangular shape, but need not be as other shapes can be used without departing from the scope of the present subject matter.

As shown in FIGS. 3A and 3C, certain exemplary embodiments include springs 325 (which can but need not be independently adjustable) to hold external lever arms 320 against the inner arms 312 and apply a force to the samples (not shown) as the external lever arms 320 bear against inner arms 312. In the exemplary embodiment shown, springs 325 are held in place with adjusting screws 326. Spring loading is adjustable by turning screws 326. In certain exemplary embodiments, loading is initially set at room temperature and adjusted for load at test temperature to compensate for spring relaxation as temperature increases. In certain exemplary embodiments, springs 325 are independently adjustable and can be set differently, while displacement and frequency can be held the same for one or more of the samples. In other exemplary embodiments, displacement, stroke length, and/or frequency can be varied, in place of or in addition to spring force adjustment.

The exemplary embodiment of FIGS. 3A, 3B and 3C includes two pairs of pivotally-connected external lever arms 320 (two long 320*a* and two short 320*b*). In certain embodiments, the lever ratio of the long and short arms is 2:1 or 2.5:1, respectively. Other ratios can be employed to change the load applied to the samples without departing from the scope of the present subject matter. In certain exemplary embodiments, one or more of the arms 312/320*a*/320*b* optionally swing outboard for quick sample change out, and in certain embodiments, one or more of external arms 320*a*/320*b* carry stationary samples (not shown) and are tensioned (loaded) by springs 325 pulling the external arms 320*a*/320*b* together.

FIG. 3D illustrates an exemplary embodiment of a holder station 310 with reciprocating samples 317*b* (also referred to as sliding samples 317*b*) held in place by self-aligning retainers 333*a* and 333*b* on sample holders 311. Bottom retainers 333*b* optionally include spring loaded threaded plungers 334 and/or set screws 335 to secure a stationary sample 317*a* in place. In the exemplary embodiment shown, top retainers 333*a* optionally include plungers (not shown) and, in certain embodiments, serve as targets for eddy current sensors (not shown) monitoring motion at the sample. Other optional features include but are not limited to threaded holes (see, e.g., FIG. 3G) of holder station 310 and vertical and/or horizontal slots for different sample orientations to accommodate various sample geometries.

Figure 3F:
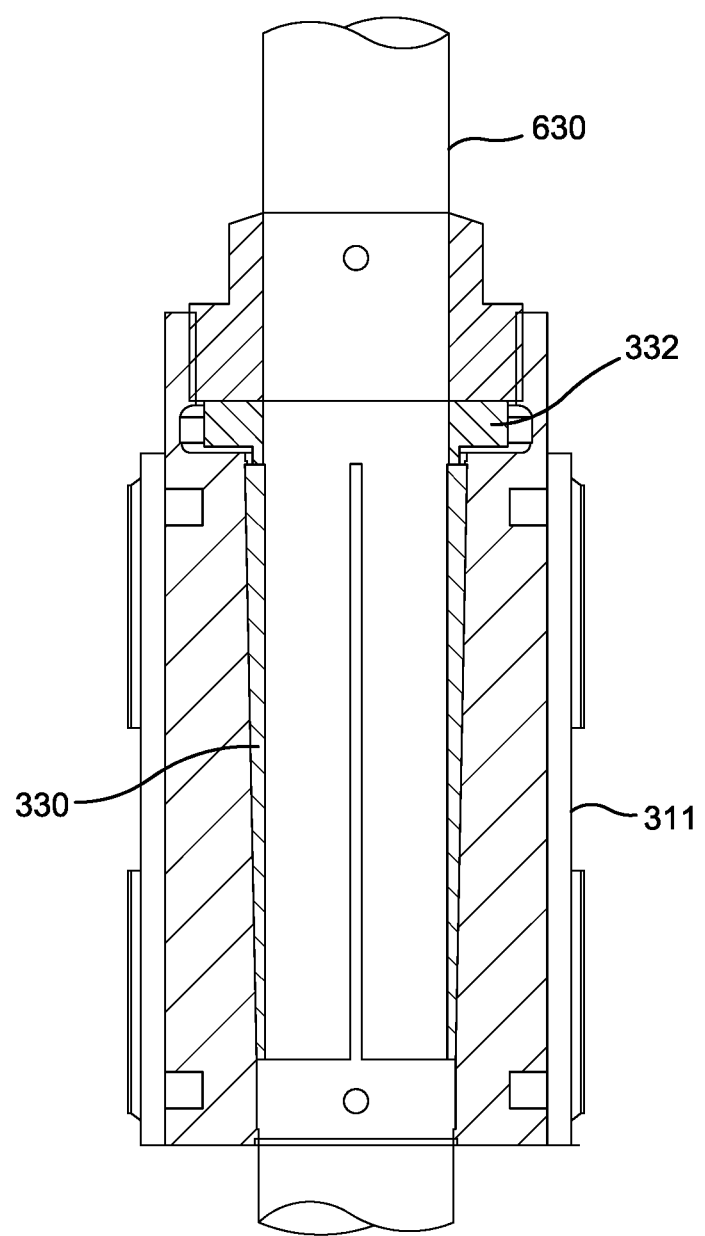
Figure 3H:
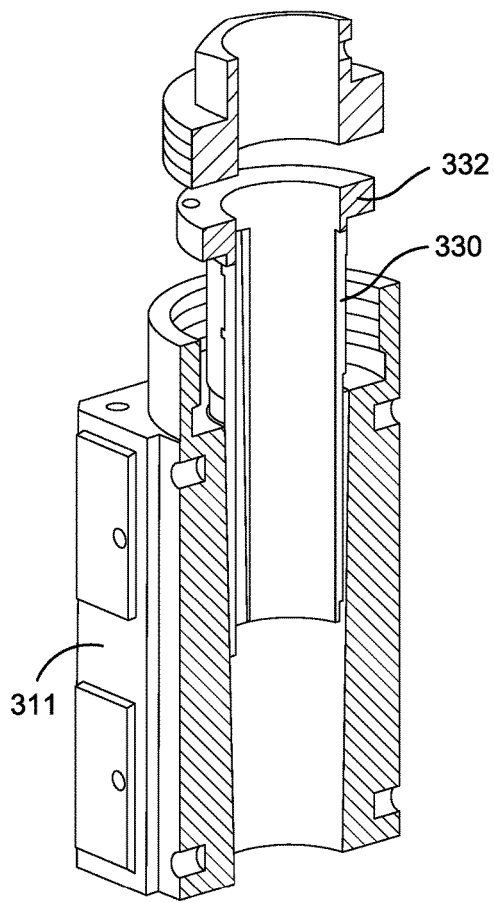
Figure 3G:
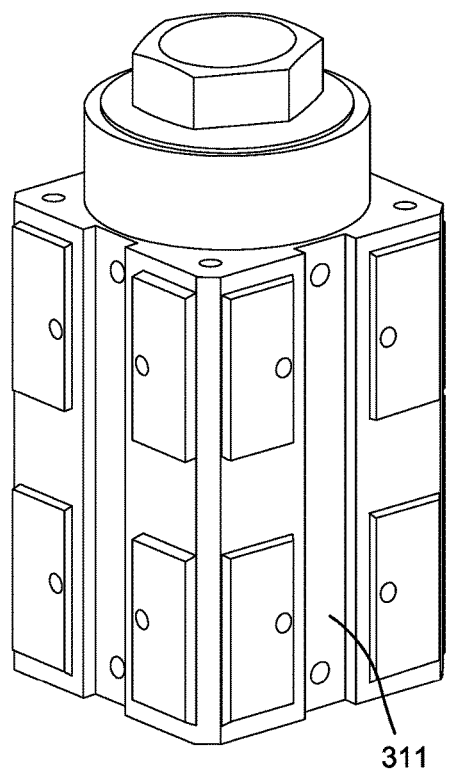

FIGS. 3F and 3H illustrate an exemplary clamping collet 330 as an exemplary way of rotationally and/or axially positioning holder station sample holder 311 at a desired stroke elevation (including, but not limited to mid-stroke elevation) such as by clamping on the lower shaft 630, optionally aligned and/or oriented with at least one inner arm sample holder 313 (as shown, for example, in FIG. 3E). In some embodiments, clamping collet 330 may be tapered while in other embodiments, clamping collet 330 is not tapered. In some embodiments, a clamping collet 330 is pushed into the hole of the sample holder 311 held in place at least in part by a locking nut 335 acting on the upper surface flange 332 of clamping collet 330. Tightening locking nut 335 generates a radial load on the lower shaft 630. In certain embodiments, collet 330 includes set screws 331 acting on at least a portion of lower shaft 630 (see, e.g., FIG. 3F). This configuration is exemplary only, as other ways known to those of skill in the art can be used to hold the sample holder in place without departing from the scope of the present subject matter.

Figure 4:
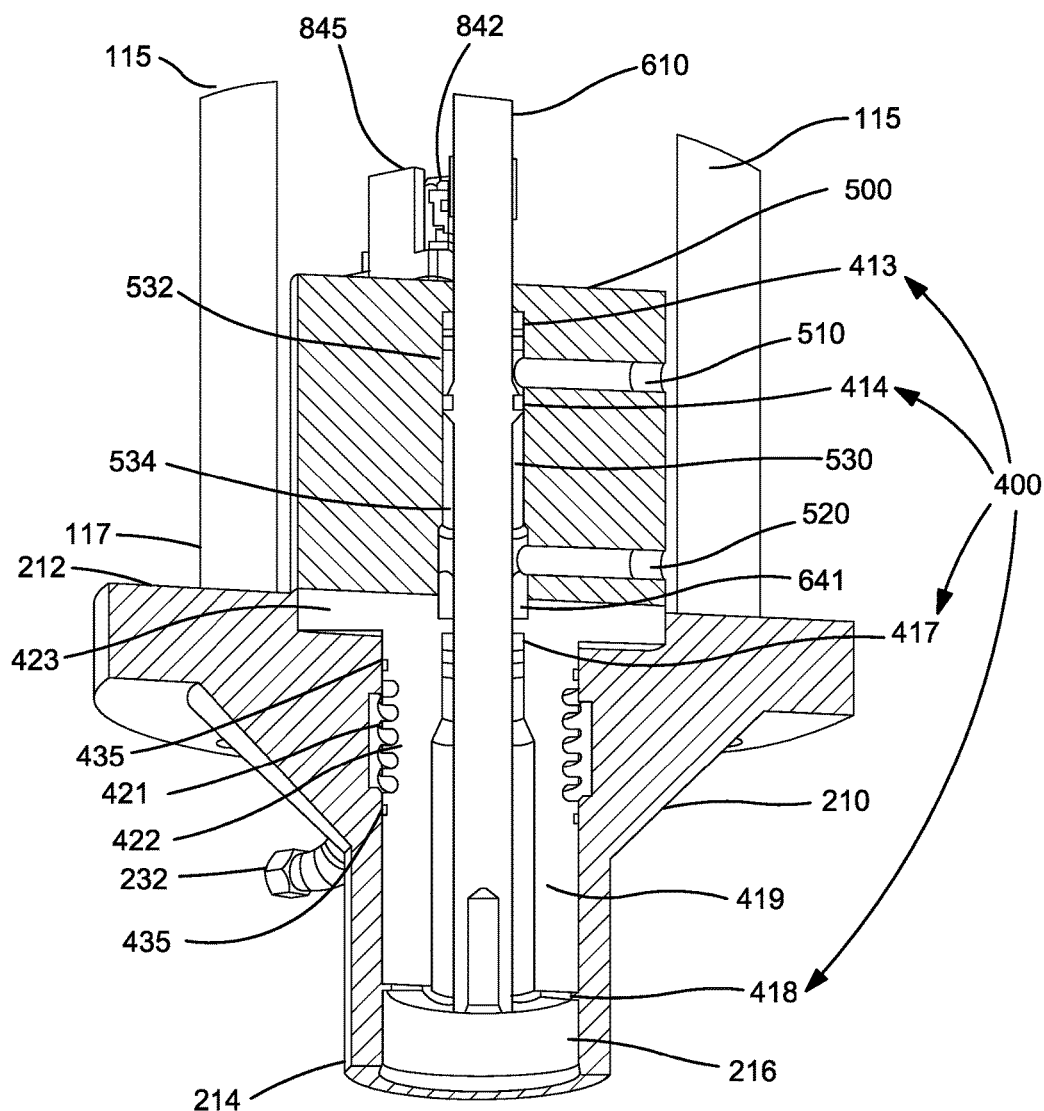
FIG. 4 illustrates an exemplary seal system.

Certain exemplary embodiments of the fretting wear test apparatus 1000 include a seal system 400, such as the exemplary seal system 400 illustrated in FIG. 4. In the exemplary embodiment of FIG. 4, seal system 400 includes upper seals 413 and 414 and lower seal 417 sealing at least a portion of the load train 600 passing through seal follower 419 and force balance assembly 500. In certain exemplary embodiments, one or more of seals 413, 414, and 417 are low friction cup seals made of a graphite-carbon filled PTFE jacket partially encapsulating a spring energizer (not shown). In certain embodiments, one or more of seals 413, 414, and 417 include a gland (not shown) with a seal jacket (not shown) expanded against the gland by pressurized fluid to help form a leak tight seal. Certain exemplary embodiments optionally include a spring (not shown) configured to provide resilience to the seal jacket and compensates for jacket wear and load train misalignment or eccentricity with respect to the force balance assembly 500. In certain exemplary embodiments autoclave pressure helps provide a seal by, for example, expanding the seal jacket.

In certain exemplary embodiments, seal system 400 includes seal follower 419 to help seal the area where load train 600 passes through autoclave adapter 210. In still other exemplary embodiments, seal system 400 includes a spiral wound gasket seal 418 between an autoclave pass through 226 and seal follower 419 mating surfaces. In the exemplary embodiment of FIG. 4, seal follower 419 is coaxially mounted inside autoclave adapter 210, and helps form a transition from autoclave head 220. Seal follower 419 is subjected to internal system pressure and a compressive load imposed by force balance assembly 500 to secure it to autoclave adapter 210.

In certain exemplary embodiments, coolant flows through an annulus 421 formed by cooling fins 422 and an inner wall of autoclave adapter 210. In these exemplary embodiments, annulus 421 is sealed by one or more radial seals 435, (which can but need not be elastomeric O-rings), which may be cooled through a cooling recirculation system (not shown) with coolant entering through inlet 232 and exiting through discharge 234.

FIGS. 4 and 5A-5D illustrate an exemplary force balance assembly 500, load train 600, and actuator assembly 700. In the exemplary embodiment shown, force balance assembly 500 is shaped as a cylinder and includes a bore 530 (see, e.g. FIG. 4) having an upper portion 522 and a lower portion 534 and configured to accommodate at least a portion of load train 600 (such as upper shaft 610 for example). The cylindrical shape is exemplary only, however, as other shapes can be used without departing from the scope of the present subject matter. In the exemplary embodiment shown, force balance assembly 500 includes a first port 510 hydraulically connected with the pressure vessel 230 and configured to equalize pressure between the pressure vessel 230 and the load train 600 and bore 530 (which can but need not be centrally located in the center of the force balance assembly 500) configured to accommodate at least a portion of upper shaft 610. The force balance assembly optionally includes second port 520 to collect any leakage through seals 414 and/or 417. In certain exemplary embodiments, force balance assembly 500 equalizes pressure on the load train 600 while providing one or more seals 413 and/or 414 against pressure from the pressure vessel 230. In certain exemplary embodiments, the force balance assembly 500 optionally includes one or more of: a seat (see, e.g., FIG. 4) for the high pressure seal 413 (which can, but need not be a low-friction cup seal); a feedback flow (not shown) configured to prevent a pumping action inherent in load cycling; a preload (not shown) to compress gasket 418 mounted between the autoclave pass through 226 and the seal follower 419; a preload (not shown) of the pressure vessel coupling 216; and a support for load train displacement sensor 845 (see, e.g., FIGS. 1 and 4). Other sensors known to those of skill in the art (including but not limited to extensometers and position sensors) can be used without departing from the scope of the present subject matter.

In the exemplary embodiments of FIGS. 5A-5D, load train 600 includes an upper shaft 610 configured to connect with an actuator 710 and passing through the force balance assembly 500, a lower shaft 630 connected to sample holder station 310 (which can but need not be reciprocating), and a coupling 620 operably connecting upper shaft 610 to actuator 710, in certain embodiments via load cell 832. In certain embodiments coupling 620 is adjustable, enabling adjustment of the distance between load cell 832 and upper shaft 610, which enables adjustment of the position of load train 600 with respect to one or more of samples 317*a* and/or 317*b* operably connected to load train 600. Certain exemplary embodiments include an enlarged collar supporting seal 414 in the region where the load train 600 passes through the force balance assembly 500 (see, e.g., FIG. 4). This collar has an area equivalent to the area of the load train lower shaft 630 inside the autoclave pressure vessel 230 to counteract the autoclave pressure. In certain embodiments, the collar includes a circumferential seat to accommodate cup seal 414.

In certain exemplary embodiments, the load train 600 is radially supported and/or guided by bearings (described below), and in certain of these exemplary embodiments, the bearings are made of Nitronic 60, a high strength stainless steel material known for its wear and galling resistance property. In certain exemplary embodiments, the region of load train 600 interfacing with the bearings is hard-faced with Stellite or equivalent hard material to prevent galling between the two sliding surfaces. It has been discovered that the combination of these two materials surprisingly and unexpectedly substantially minimize galling between the contacting surfaces also after long term cycling (approximately 250 million cycles, for example) making them ideal for combating abrasive wear and fretting in high temperature environments. In certain exemplary embodiments the bearings include an upper bearing 641 (see, e.g., FIG. 4), an intermediate bearing 642 (FIGS. 2 and 5B), and a lower bearing 643 (FIGS. 2 and 5B). The bearings limit lateral motion and/or rotation of load train 600 during fretting. In certain exemplary embodiments lower bearing 643 has a polygon profile 724 (see, e.g., FIG. 5D), intermediate bearing 642 is hourglass-shaped and configured to align the load train 600 between the upper and lower plates 112 and 124, and upper bearing 641 is a linear bearing with a larger diametrical clearance than the other bearings to compensate for any misalignment of load train 600 with respect to the top flange 423 of seal follower 419 (see, e.g., FIG. 4).

In certain exemplary embodiments, lower shaft 630 is supported by lower and intermediate bearings 643 and 642 and rests on a film of pressurized liquid (not shown) drawn by a pumping action from reciprocating load train motion and used to minimize friction on load train 600. This allows bearings to have a very low coefficient of friction with minimal long term wear under high cycling conditions. In the exemplary embodiment of FIGS. 5B-5D, for example, lower bearing 643 interfaces with an end 670 (which can but need not be polygonally-shaped) of lower shaft 630 to allow sliding, but impede rotation. Other bearing shapes and/or other numbers of bearings can be used without departing from the scope of the present subject matter.

Figure 5A:
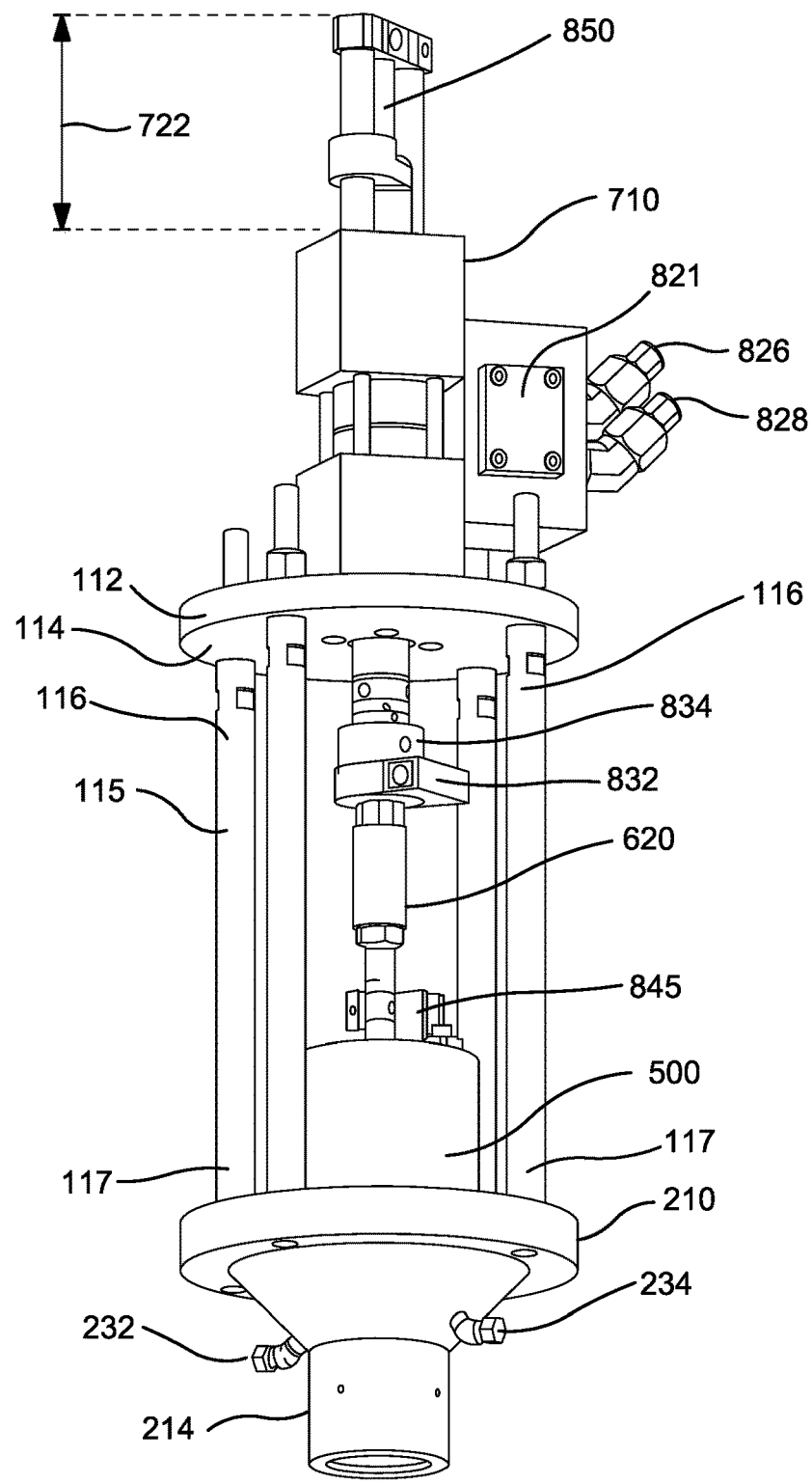

In the exemplary embodiment of FIGS. 1 and 5A, actuator 710 mounts to the second side 114 of upper plate 112 which is supported by and/or operably connects with autoclave adapter 210. The upper tie rods 115 transfer at least a portion of the load generated by the actuator 710 to autoclave adapter 210. Actuator 710 connects to load cell 832 and optionally includes load cell adapter 834. Adapter 834 connects with load train 600 and can be preloaded, which helps minimize the load train backlash and therefore helps minimize "false fretting" of the samples. In certain embodiments actuator 710 includes an upper anti-rotation assembly 722 and/or a lower anti-rotation assembly 724 (see, e.g., FIGS. 1 and 5D) which help prevent rotation of load train 600.

In certain exemplary embodiments, actuator 710 is a fatigue rated, double-acting servo-hydraulic actuator with a force capacity of 5,000 pounds (22 kN) configured to produce micron-range displacements at frequencies of up to 150 Hz. In a sliding configuration, actuator 710 is configured to provide up to a 500 micron peak-to-peak displacement to load train 600. In the exemplary embodiment shown, actuator 710 moves the reciprocating sample(s) 317*b* via holder 311 and/or generates fretting motion via load train 600 connected to holder station 310, which can but need not be reciprocating. In certain exemplary embodiments actuator 710 is hydraulic. The actuators discussed are exemplary only, as other actuators known to those of skill in the art can be used without departing from the scope of the present subject matter.

Figure 6:
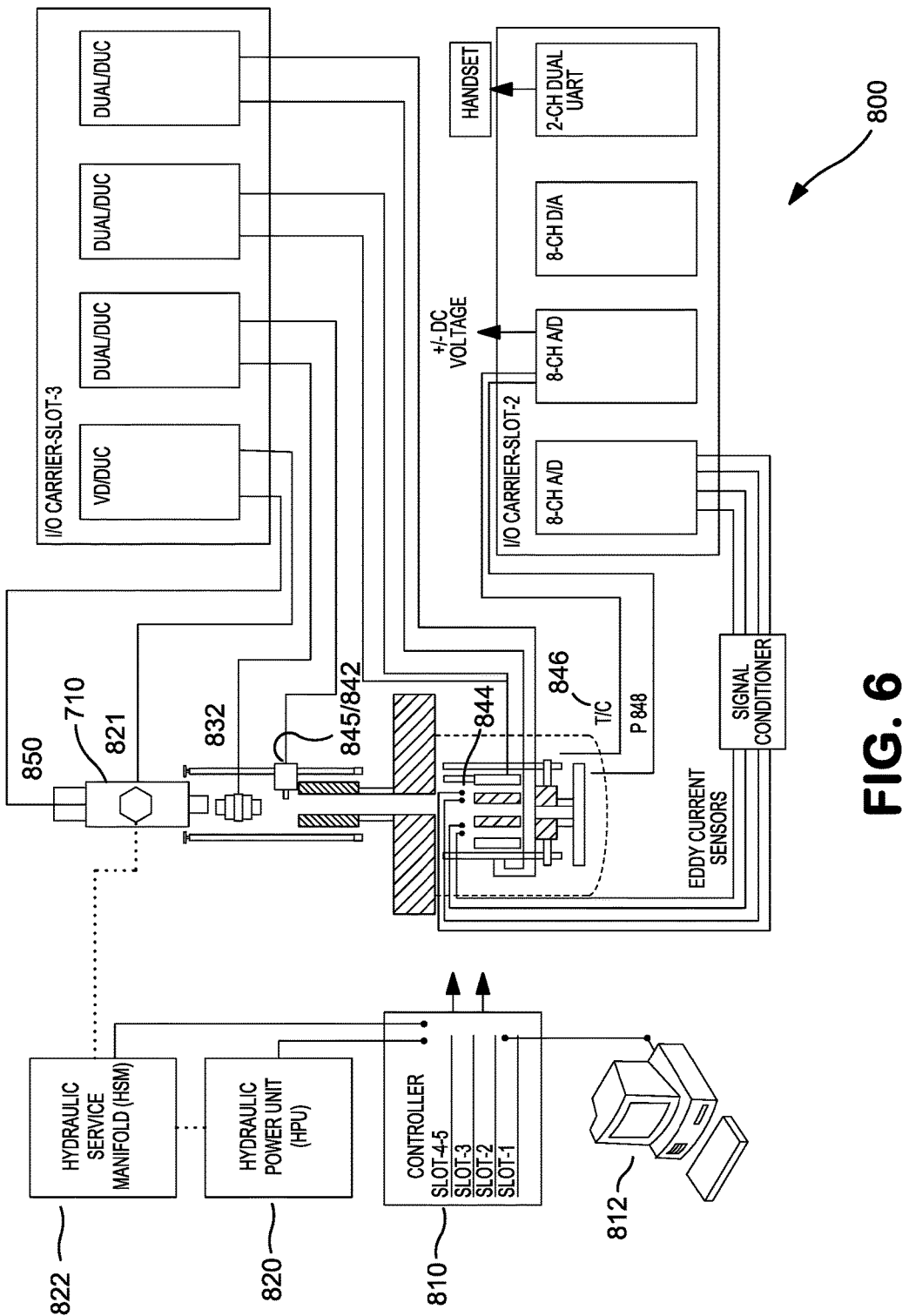
FIG. 6 illustrates an exemplary control system.

FIG. 6 illustrates an exemplary control system 800. The items in this exemplary control system 800 are implemented using software, firmware, hardware, and/or a combination thereof. In certain exemplary embodiments, calculations are implemented by electronic circuits hardwired to perform these calculations, and/or at least one microcontroller. Calculations may be implemented wholly or in part using software as an executable program in a non-transitory computer-readable medium executed by a general or specially-purposed computer, such as a personal computer, workstation, minicomputer, or mainframe computer, generally referred to as a computer.

The computer may be windows-based and/or use any other operating system known to those of skill in the art. The computer at least partially implements the modules and elements described below with one or more computer processors, memory coupled to a memory controller, and one or more input and/or output (I/O) device(s) (peripheral(s)). Examples of the input/output controller include, but are not limited to, one or more buses or other wired or wireless connections. The input/output controller may have additional elements (omitted for simplicity) such as controllers, buffers (caches), drivers, repeaters, and receivers, to enable communications. Further, the device(s) may include address, control, and/or data connections to enable appropriate communications among the aforementioned components. When the systems and methods described herein are implemented in software, the methods are stored on any non-transitory computer readable medium for use by or in connection with any computer related system or method. The software in the non-transitory computer-readable medium may include one or more separate programs, and may be in the form of a source program, executable program (object code), script, or any other entity comprising a set of instructions to be performed.

The exemplary embodiment shown includes a controller 810 (which can but need not be a single channel controller) which provides real-time closed-loop control, with sensor signal conditioning and function generation to drive actuator 710. At least one of the magnitude, frequency and offset direction of loading are dictated by a forcing function supplied by a signal generator 812 using selectable waveforms generated by controller software. An external forcing function is adjustable to desired amplitude through a feedback control loop using extensometer 845 to determine the stroke length experienced by the sample(s) under test. Other sensors known to those of skill in the art (including but not limited to position sensors and displacement sensors) can be used without to determine stroke length without departing from the scope of the present subject matter. In certain exemplary embodiments, real-time signal monitoring as well as data acquisition of measured parameters is available.

Control system 800 optionally includes signal conditioning for one or more positioning and/or load sensors. In certain embodiments, eddy current displacement sensors 844 (FIGS. 2 and 6), optionally mounted inside the pressure vessel 230, monitor relative displacement between samples. In addition to and/or in place of these sensors, other exemplary embodiments include load cells 832 (see, e.g., FIGS. 1, 5A, and 6) configured to monitor force applied to samples. Other exemplary embodiments include an extensometer 845 configured to monitor displacement of the reciprocating motion, and/or load cell 832 configured to monitor load applied by actuator 710 to load train 600. In certain exemplary embodiments, linear-variable differential transformer (LVDT) 850 (see, e.g., FIGS. 1, 5A, and 6) controls load train displacement via a feedback loop with servo valve 821. Other control methods can be used without departing from the scope of the present subject matter. In the exemplary embodiment shown, servo valve 821 controls the amount of hydraulic fluid and the speed and direction of load train movement. In embodiments with a hydraulic actuator, hydraulic fluid is supplied to the actuator inlet 826 (FIG. 5A, for example) via manifold 822 (which can but need not be a dual-station manifold) connected to a power unit 820 (shown schematically in FIG. 6, which can but need not be hydraulic). Actuator discharge 828 opens to a return line (not shown) causing actuator 710 to extend or retract. In certain exemplary embodiments, closed loop feedback is provided by a sensor via, for example, LVDT 850 (coarse) and/or extensometer 845 (fine). An exemplary alternate position sensor is a non-contact capacitive sensor (not shown) mounted in the same location or in vicinity of extensometer 845. In still other embodiments, temperature and/or pressure sensors 846/848 monitor operation and/or are independently controlled to maintain high temperature pressurized conditions inside the autoclave pressure vessel 230 and, in certain exemplary embodiments, shut down the system if abnormal conditions occur. Other control mechanisms and configurations known to those of skill in the art can be used without departing from the scope of the present subject matter.

Conclusion

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:
1. A test apparatus, comprising:
an autoclave head;
a fretting mechanism connected on a first end of the fretting mechanism to a first side of the autoclave head;
a load train operably connected with the first end of the fretting mechanism;
an autoclave adapter connected on a first side of the autoclave adapter to a second side of the autoclave head; and
a force balance assembly connected to the second side of the autoclave head and configured to equalize a pressure acting on the load train;
wherein the fretting mechanism further comprises:
a holder station configured to connect to the load train and having at least two sample holders;
at least two pivoting inner lever arms having at least two opposing sample holders configured to contact with the holder station sample holders; and
at least two pivoting external lever arms configured to contact with the at least two inner lever arms.
2. The test apparatus of claim 1, further comprising:
an upper plate;
a plurality of upper tie rods each having a first end and a second end, each first end connected to a first side of the upper plate and each second end connected to a second side of the autoclave adapter;
a lower plate;
a plurality of lower tie rods having a first end and a second end, each first end connected to a first side of an intermediate plate and each second end connected to a first side of the lower plate; and a pressure vessel sealingly connected to the first side of the autoclave head.

3. The test apparatus of claim 1, wherein the force balance assembly further comprises:
a first port hydraulically connected with a pressure vessel and configured to equalize pressure between the pressure vessel and at least a portion of the load train;
a central bore configured to accommodate the load train;
an upper pressure seal on an upper portion of the central bore and configured to sealingly connect with the load train; and
a lower pressure seal on a lower portion of the central bore and configured to sealingly connect with the load train.

4. The test apparatus of claim 1, wherein the holder station further comprises at least one self-aligning sample holder secured to one of the pivoting inner lever arm opposing sample holders.

5. The test apparatus of claim 4, wherein at least one self-aligning sample holder further comprises a pivot point.

6. The test apparatus of claim 1, wherein the load train comprises:
an upper shaft configured to connect with an actuator and passing through the force balance assembly;
a lower shaft connected to a reciprocating sample holder; and
a coupling adjustably connecting the upper shaft with an actuator.

7. The test apparatus of claim 6, further comprising at least three bearings configured to support the load train.

8. The test apparatus of claim 6, further comprising:
a first anti-rotation device connected to a first end of the load train; and
a second anti-rotation device connected to a second end of the load train.

9. A test apparatus, comprising:
a support structure;
a load train connected at a first end of the load train to a first end of the support structure;
a fretting mechanism operably connected to a second end of the load train;
a force balance assembly having a first load train pass through on a first end, wherein the force balance assembly is configured to equalize a pressure acting on the load train;
a pressure vessel adapter having a second load train pass through and connected on a first end of the pressure vessel adapter to a second end of the force balance assembly; and
a pressure vessel sealingly connected to a second end of the pressure vessel adapter;
wherein the fretting mechanism further comprises:
a holder station configured to connect to the load train and having at least two sample holders;
at least two pivoting inner lever arms having at least two opposing sample holders configured to contact with the holder station sample holders; and
at least two pivoting external lever arms configured to contact with the at least two inner lever arms.

10. The test apparatus of claim 9, wherein the pressure vessel encloses a sample station.

11. A method of testing fretting wear, comprising:
placing a test sample in a fretting mechanism, the fretting mechanism having a holder station configured to connect to a load train and having at least two sample holders, at least two pivoting inner lever arms having at least two opposing sample holders configured to contact with the holder station sample holders, and at least two pivoting external lever arms configured to contact with the at least two inner lever arms;
contacting the test sample with an opposing sample in an opposing sample holder; and
applying a reciprocating motion to the test sample with the test sample in contact with the opposing sample.

12. The method of claim 11, further comprising varying at least one of a frequency, force, and stroke length of the reciprocating motion.

13. The method of claim 11, further comprising the step of placing the test sample in a pressurized environment.

14. The method of claim 13, further comprising the step varying a pressure of the pressurized environment.

15. The method of claim 13, further comprising the step varying a temperature of the pressurized environment.

16. A test apparatus, comprising:
an autoclave head;
a fretting mechanism connected on a first end of the fretting mechanism to a first side of the autoclave head and having a plurality of independently adjustable pivoting lever arms having sample holders, wherein the lever arms are configured to contact a plurality of samples with a plurality of opposing samples;
an adjustable stroke length load train operably connected on a first end of the load train with the first end of the fretting mechanism and connected on a second end of the load train with a linear-variable differential transformer actuator;
an autoclave adapter connected on a first side of the autoclave adapter to a second side of the autoclave head; and
a force balance assembly connected to the second side of the autoclave head and configured to equalize a pressure acting on the load train.

17. The test apparatus of claim 16, further comprising at least one self-aligning sample holder secured to one of the plurality of independently adjustable pivoting lever arms.

* * * * *